United States Patent
Levin

(10) Patent No.: US 7,162,290 B1
(45) Date of Patent: Jan. 9, 2007

(54) METHOD AND APPARATUS FOR BLOOD GLUCOSE TESTING FROM A REVERSIBLE INFUSION LINE

(75) Inventor: Paul D. Levin, Santa Cruz, CA (US)

(73) Assignee: Palco Labs, Inc., Scotts Valley, CA (US)

( * ) Notice: Subject to any disclaimer, the term of this patent is extended or adjusted under 35 U.S.C. 154(b) by 0 days.

(21) Appl. No.: 11/228,827

(22) Filed: Sep. 16, 2005

(51) Int. Cl.
    *A61B 5/05* (2006.01)
(52) U.S. Cl. .................. 600/345; 600/347; 600/385
(58) Field of Classification Search ............... None
    See application file for complete search history.

(56) References Cited

U.S. PATENT DOCUMENTS

| 3,832,067 | A | | 8/1974 | Kopf et al. |
|---|---|---|---|---|
| 3,910,256 | A | | 10/1975 | Clark et al. |
| 4,573,968 | A | | 3/1986 | Parker |
| 5,165,406 | A | | 11/1992 | Wong |
| 5,206,711 | A | * | 4/1993 | Berthold et al. ............ 356/436 |
| 5,758,643 | A | | 6/1998 | Wong et al. |
| 5,947,911 | A | | 9/1999 | Wong et al. |
| 2004/0015158 | A1 | | 1/2004 | Chen et al. |
| 2004/0019280 | A1 | | 1/2004 | Waner et al. |

\* cited by examiner

*Primary Examiner*—Robert L. Nasser
(74) *Attorney, Agent, or Firm*—Bruce H. Johnsonbaugh

(57) ABSTRACT

A method and apparatus for periodically and automatically testing and monitoring a patient's blood glucose level. A disposable testing unit is carried by the patient's body and has a testing chamber in fluid communication with infusion lines and a catheter connected to a patient blood vessel. A reversible peristaltic pump pumps the infusion fluid forwardly into the patient blood vessel and reverses its direction to pump blood into the testing chamber to perform a glucose level test. The presence of blood in the testing chamber is sensed by a LED/photodetector pair or pairs and when the appropriate blood sample is present in the test chamber, a glucose oxidase electrode is energized to obtain the blood glucose level. The resulting glucose level is displayed on a monitor. The unit is typically used for a patient in an intensive care unit.

6 Claims, 12 Drawing Sheets

METHOD AND APPARATUS FOR BLOOD GLUCOSE TESTING FROM A REVERSIBLE INFUSION LINE

BACKGROUND AND SUMMARY OF INVENTION

This invention relates to blood glucose testing in critically ill patients. The need for a convenient and easily applied method of glucose monitoring in the Intensive Care Unit became evident after the landmark study of Van den Berghe and colleagues published in the Nov. 8, 2001 issue of *The New England Journal of Medicine*.

This paper demonstrated an overall reduction in ICU (intensive Care Unit) patient mortality of 34% when blood glucose was kept in the 80 to 110 mg per deciliter range. Samples were taken from an arterial line at 1 to 4-hour intervals and sent to the hospital lab for analysis. In the intensive therapy group, an insulin infusion was started if blood glucose exceeded 110 mg per deciliter and was adjusted to maintain normal blood glucose levels. A virtual flood of articles have since appeared and confirm improved outcomes in the treatment of various critical conditions including infection, stroke, in patients undergoing coronary bypass surgery, and in the treatment of myocardial infarction in both diabetic and non-diabetic patients. One study showed greatly improved outcomes when diabetics were monitored and treated intensively with insulin in the hospital for three days prior to undergoing coronary bypass surgery.

Intensive treatment with insulin requires knowledge of patient blood sugar levels which presently involves obtaining either an arterial or a venous blood sample or pricking the patient's finger from time to time to obtain a capillary blood sample. Capillary samples are placed on a strip and read using a home-type glucose meter. All of these methods require considerable nurse or technician time. In the U.S. at present only 20% to 30% of patients in the ICU have arterial lines. Many patients, especially non-diabetics, find repeated finger sticks objectionable. Furthermore, intermittent blood samples may not be done often enough to give an accurate picture of blood sugar levels.

Attempts have been made in the past to automatically monitor blood analytes, especially blood gases. Most method have involved reversing the direction of blood flow in an infusion line so that blood is pulled out of the patient's circulation at intervals, analyzed and then re-infused back into the patient by changing the direction of flow. This method was possibly first described by Clark in U.S. Pat. No. 3,910,256 who used saline flushes between samples and whose method had means for detecting air in the blood which resulted in an alarm and shutting down the infusion.

Parker in U.S. Pat. No. 4,573,968 describes a system in which an infusion pump reverses direction to draw a patient blood sample through a catheter into contact with one or more electrochemical sensors. A compact cassette near the patient carries the sensors.

Wong and Associates in U.S. Pat. Nos. 5,165,406; 5,758,643 and 5,947,911 describe a system again using a peristaltic pump to move infusion fluid and blood back and forth through the system. Sensing is done by a cassette which is placed on the patient's forearm.

In U.S. Pat. No. 5,758,643 Wong and Associates determine the arrival of blood in the area of the sensors by reading the signals from the sensors, themselves, and ascribe particular importance to a calcium sensor. The system is programmed to activate an alarm and switch off the infusion pump if the arrival of the patient's blood sample in the area of the sensors has not been detected by a predetermined time. In U.S. Pat. No. 5,947,911 Wong's group describes methods for reducing the volume of the purging fluid following the taking of a sample.

All of the systems mentioned have a level of complexity which makes manufacturing of the devices expensive and their practical application difficult and time consuming. Via Medical, now a division of International Biomedical of Austin, Tex., manufactures and sells the device designed by Wong and Associates. It uses a large patient monitor and a cassette-type analyzer on the patient's forearm. Cost of the disposables for each patient use is approximately $300 for either blood gases or blood glucose. Set-up time is fifteen to twenty minutes.

What is clearly needed is a system for hospitalized patients which is affordable and uncomplicated. The present invention eliminates the difficulties and complexities of previously described devices using a novel method of blood sampling located close to the catheterized artery or vein.

A problem encountered in reversing an infusion line for sampling is determining how much blood should be withdrawn in order to be certain that pure undiluted blood is in contact with the sensor. This problem is discussed in U.S. Pat. No. 5,758,643 by Wong and Associates who attempt to solve the problem with the sensors themselves and particularly a calcium sensor which presumably will register a blood calcium in a normal range when undiluted blood has reached the sensing area. This method, while fairly satisfactory, may be somewhat inaccurate unless the patient's actual blood calcium level is exactly known. Also, there may be some delay between the time an undiluted sample reaches the sensing area and the time that a normal value is registered by the sensor and transmitted to the monitor which contains the pump. As a result, an unnecessarily large amount of blood may be withdrawn prior to stopping the peristaltic pump which is pumping in a retrograde manner to remove blood from the patient's catheter.

The present invention discloses a novel method of halting the withdrawal of blood at the proper time so that a pure undiluted sample is presented to the sensor and ensures that no more than the necessary amount of blood is withdrawn. In the method to be described, at least one, and for optimum performance two, LED/photodetector pairs are placed adjacent to the sampling chamber. In the present invention, the change from clear fluid to blood within the sampling chamber will cause a fairly sudden drop in the amount of light crossing the chamber since red cells will block considerable light in contrast to ordinary infusion fluid which is clear. The area of transition will be smeared out to a greater or lesser extent depending on the speed of the infusion and the size of the catheterized blood vessel. If the infusion was rapid, for example several hundred milliliters per hour, the transition area may extend for 10 to 20 cm up the blood vessel. If very little fluid was being infused, the withdrawal of a fluid column of just a few centimeters may suffice to place a pure blood sample into the sampling chamber. The disposable device, with an LED/photodetector pair at each end of the sampling chamber, can readily detect when pure or undiluted blood fills the entire chamber because light reaching the photodetectors will be equivalent. It is at this moment, when equal amounts of light are received by the photodiodes, that the reverse motion of the peristaltic pump inside the bedside monitor can be stopped and the blood level of glucose tested.

Following testing, the peristaltic pump is again run in the normal forward direction to resume the infusion at the rate set by the caregiver.

The present invention contains no expensive parts and can be made economically to allow wide use of the invention among critically ill hospitalized patients. The disposable test unit is relatively small and can be worn with comfort by the patient on the mid-forearm with the vessel catheter crossing the wrist to be inserted, in most cases, in a small vein on the back of the hand. Catheters of this type are commonly used for infusion lines and can be inserted by virtually all medical personnel who care for the critically ill.

The catheter may be inserted elsewhere as well and the device can be used with arterial lines or central venous catheters. It is particularly useful in the latter case since dilution of venous blood in a central line may extend quite high up the arm. Regardless of the amount of dilution, the invention will be able to discern when a pure blood sample has reached the sampling chamber.

The disposable test unit is built up from four layers of plastic and, when the layers are joined in final assembly, the device measures approximately 56 mm×30 mm×11 mm (2.25×1.25×0.440 inches). The layers are each 2.5 to 3.0 mm thick and allow features such as the sampling chamber to be molded into the thin layers of plastic. The flex circuit carrying the glucose sensor is located between layers 2 and 3. The flex circuit carrying the LEDs is mounted between layers 1 and 2, and the flex circuit carrying the photodetectors is mounted between layers 3 and 4. The four layers are welded together ultrasonically to produce in the final assembly a water tight hermetically sealed device.

The glucose sensing area of the disposable device contains a glucose oxidase electrode with an active area of about 25 square millimeters. The glucose electrode is affixed to the distal area of the flex circuit and is covered by a thin polyurethane membrane which prevents cells and proteins from interfering with the action of the enzyme. An advantage of sampling intermittently, for example once every five minutes, is that during the period of ordinary fluid infusion, the membrane is cleared of cells and proteins which may have temporarily lodged on the membrane but are washed off by the infusion fluid between tests so that the possibility of membrane clogging by proteins or cells is greatly reduced. A suitable glucose oxidase electrode for such a flex circuit is made by Conductive Technologies of York, Pa.

The disposable test unit is provided on its front surface with a male Luer fitting to take the female end of a polyethylene blood vessel catheter. The infusion line and electric cable carrying the electric leads are attached to the opposite face of the test unit with the infusion line being terminated at a drip chamber which inserts into a standard IV fluid bag. The cable carrying the electronic leads from the various flex circuits attached to an appropriate receptacle on the monitor.

The infusion line is provided near its upper extremity with a short segment of soft silicone tubing to facilitate its use with a peristaltic pump. A door at the front of the monitor allows the caregiver to place the silicone portion of the infusion tubing next to the pump roller, and closure of the door on the front of the monitor locks the tubing in place against the roller wheel of the pump. A small peristaltic pump suitable for this application is made by Watson-Marlow Bredel of Commerce, Colo.

Calibration can be accomplished daily or as often as needed by stopping the pump and injecting calibration fluid into the sampling chamber through a Luer-activated valve close to the chamber. During calibration, the glucose electrode reads the glucose value of the solution and, if necessary, resets the electronic look-up table in the monitor to reflect the known value of the calibration solution.

A primary object of the invention is to provide a low cost, disposable and simple device for automatically monitoring blood glucose levels in hospitalized patients.

A further object of the invention is to provide a simple but yet reliable system for determining when an undiluted sample of blood is present in a test chamber prior to testing the sample for its blood glucose level.

Other objects and advantages will become apparent from the following description and drawings.

DETAILED DESCRIPTION OF THE DRAWINGS

Figure 1:
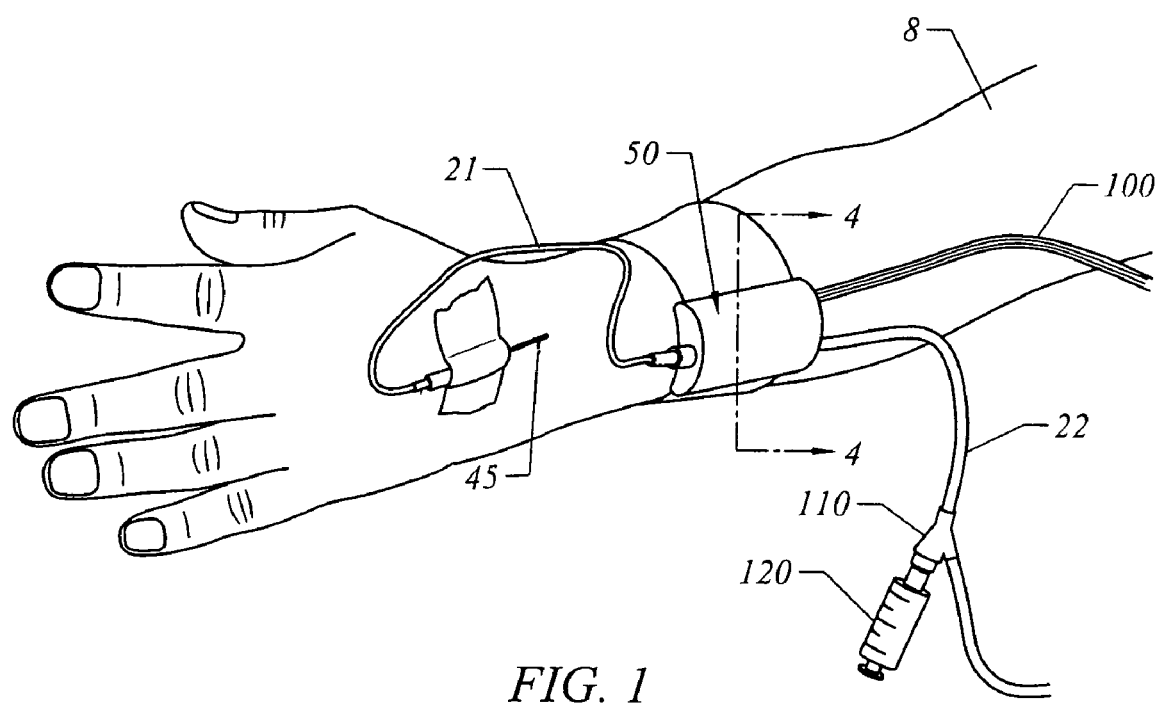
FIG. 1 is a perspective view of a portion of the device attached to a patient's forearm, showing a catheter inserted into a patient blood vessel.
Figure 2:
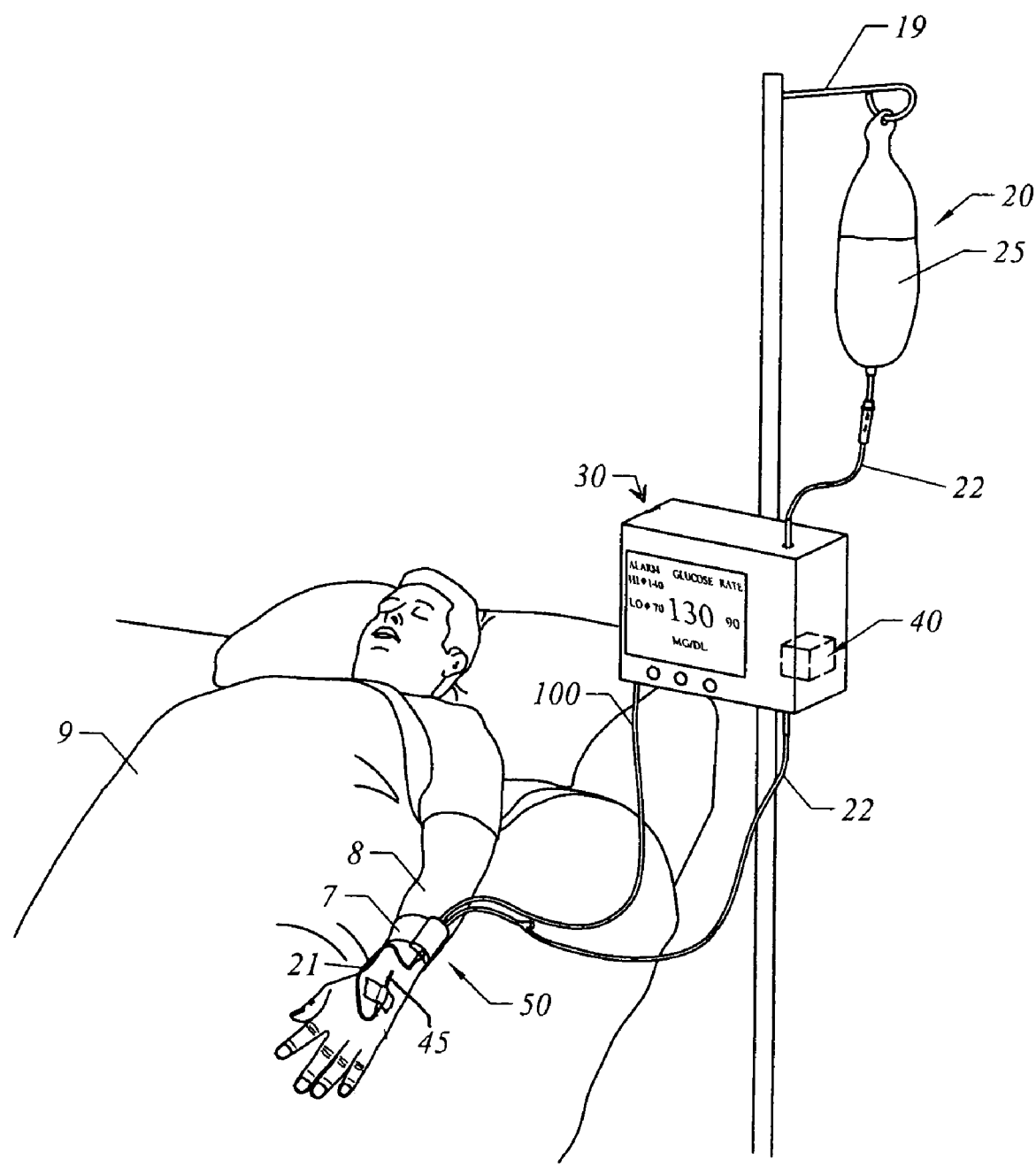
FIG. 2 is an overall perspective view showing the present invention attached to a hospitalized patient.

FIGS. 1 and 2 illustrate the overall environment of the invention. A hospitalized patient 9, typically in an ICU unit, is shown with a disposable testing unit 50 of the present invention attached to his forearm 8 by a Coban elastic band 7. A catheter 45 is shown inserted into a patient blood vessel on the back of the patient's hand. A first infusion line 21 connects catheter 45 to testing unit 50.

A source of infusion fluid is shown as IV bag 20 suspended from a support 19 as is known in the art. Infusion fluid 25 stored in infusion bag 20 passes downwardly through a second infusion line 22 and through a reversible peristaltic pump 40 carried in monitor housing 30. The second infusion line 22 continues downwardly from peristaltic pump 40 and enters the test unit 50. The infusion fluid passes through testing unit 50 as described in detail below and through first infusion line 21 that extends from testing unit 50 to catheter 45 and provides infusion fluid into the patient's blood vessel. When the reversible peristaltic pump 40 is operating in its ordinary forward motion, infusion fluid 21 from infusion source 20 is pumped through second infusion line 22 through testing unit 50 and through first infusion line 21 into the patient's blood vessel. In order to obtain a blood sample and test for blood glucose levels, the peristaltic pump is reversed and pumps infusion fluid and blood backwardly through test unit 50 until an undiluted blood sample is available for testing, as described in further detail below.

Electrical power is fed to test unit 50 by line 100 extending from monitor 30. A Luer fitting 110 is placed in infusion line 22 near test unit 50. A syringe 120 is inserted into Luer fitting 110 for periodic calibration with a reference solution.

Figure 3:
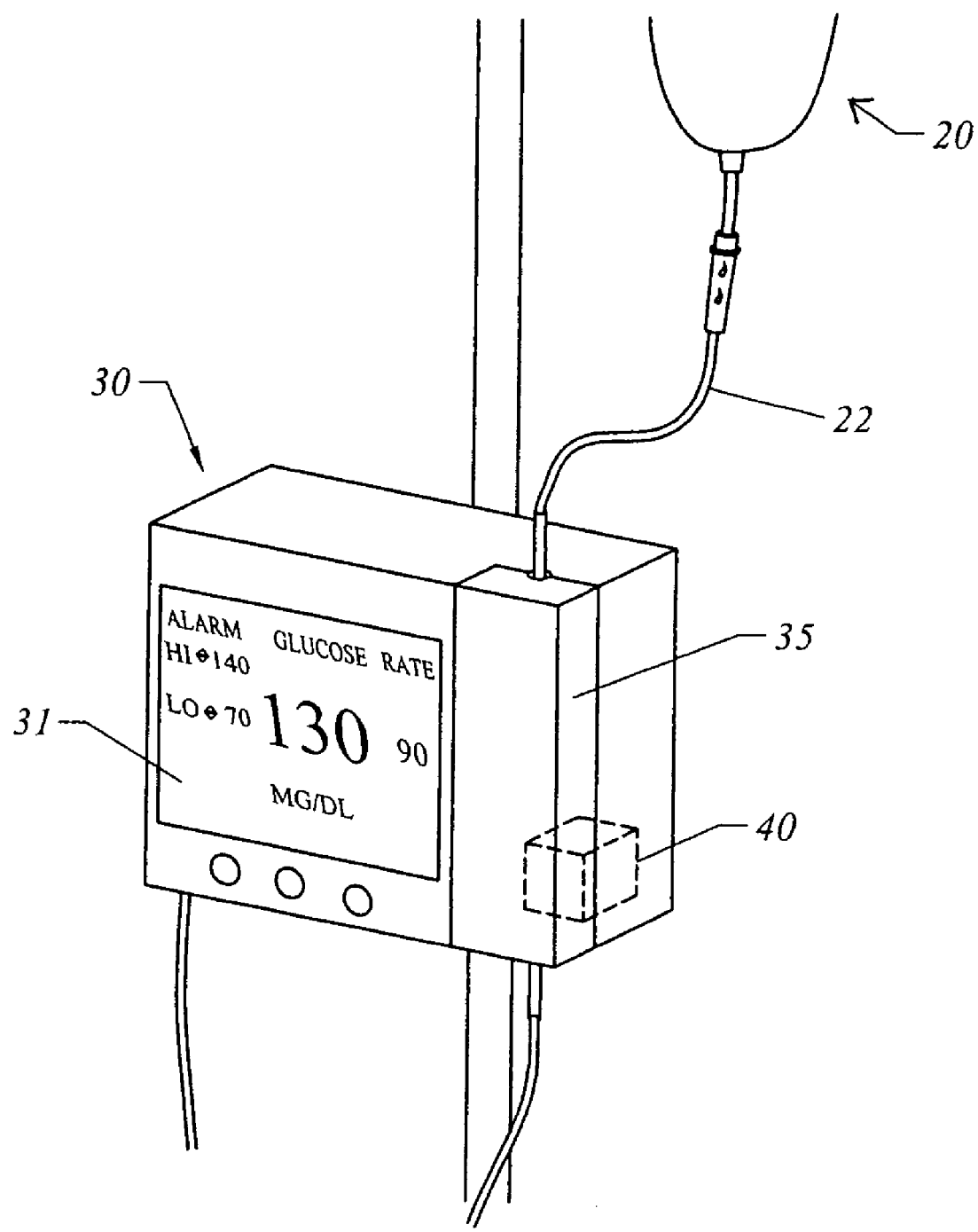
FIG. 3 is a perspective view of the monitor utilized with the invention, wherein the monitor housing houses a reversible peristaltic pump.

FIG. 3 illustrates the monitor 30 having a screen 31 that displays the blood glucose level from the most recent test. The screen 31 also preferably displays blood pressure and pulse rate. An access door 35 located adjacent screen 31 opens to allow access to peristaltic pump 40 (shown in phantom) for placement of or removal of the disposable infusion line 22.

Figure 4:
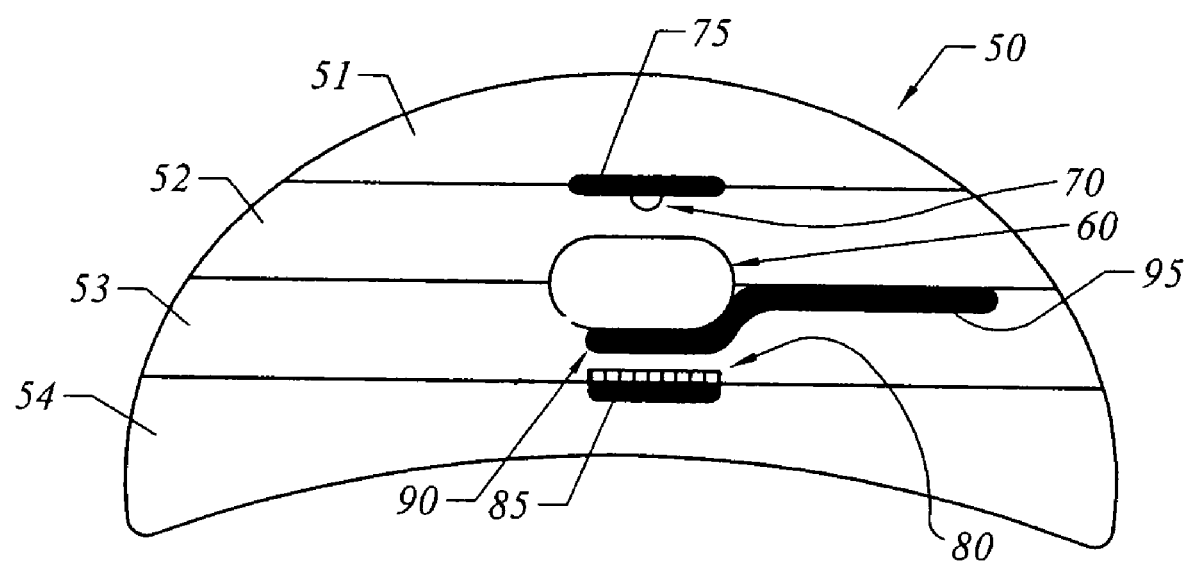
FIG. 4 is a sectional view on the line 4—4 of FIG. 1.

The operation of the testing unit 50 is shown best in FIG. 4 which is a sectional view through the center of testing unit 50. Testing unit 50 in its preferred form includes a plurality of four plastic molded layers 51–54. A test chamber 60 is formed between adjacent plastic layers 52 and 53, which are transparent. A light source 70 is mounted between plastic layers 51 and 52 and adjacent test chamber 60. Light source 70 is preferably a LED but may be other light sources known in the art. Light source 70 is energized by a flexible circuit 75.

A photodetector 80 is mounted between plastic layers 53 and 54 on the opposite side of test chamber 60 from light source 70. Photodetector 80 is energized by flexible circuit 85.

A blood glucose tester 90 is carried by plastic layer 53 immediately adjacent testing chamber 60. The blood glucose testing means 90 is preferably a glucose oxidase electrode 91 as known in the art. Electrode 91 is energized by flexible circuit 95.

Referring to FIG. 4, when it is desired to perform a test of the patient's blood glucose level, the peristaltic pump 40 is reversed and infusion fluid combined with blood begins moving backwardly through first infusion line 21 through testing unit 50 and through testing chamber 60.

Figure 5:
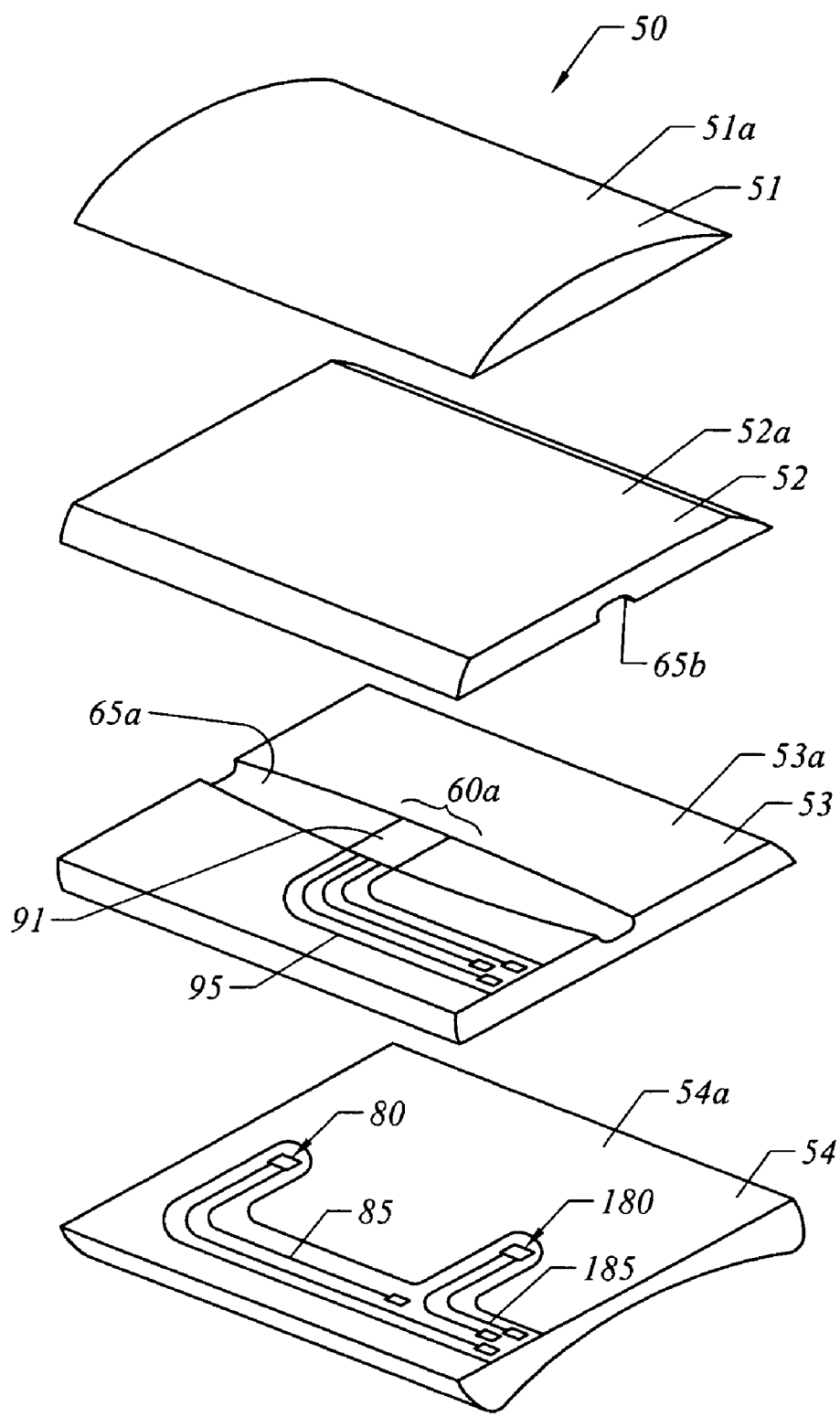
FIG. 5 is an exploded view of the four layers utilized in the preferred form of the invention, looking downwardly at an angle at each of the four layers.
Figure 6:
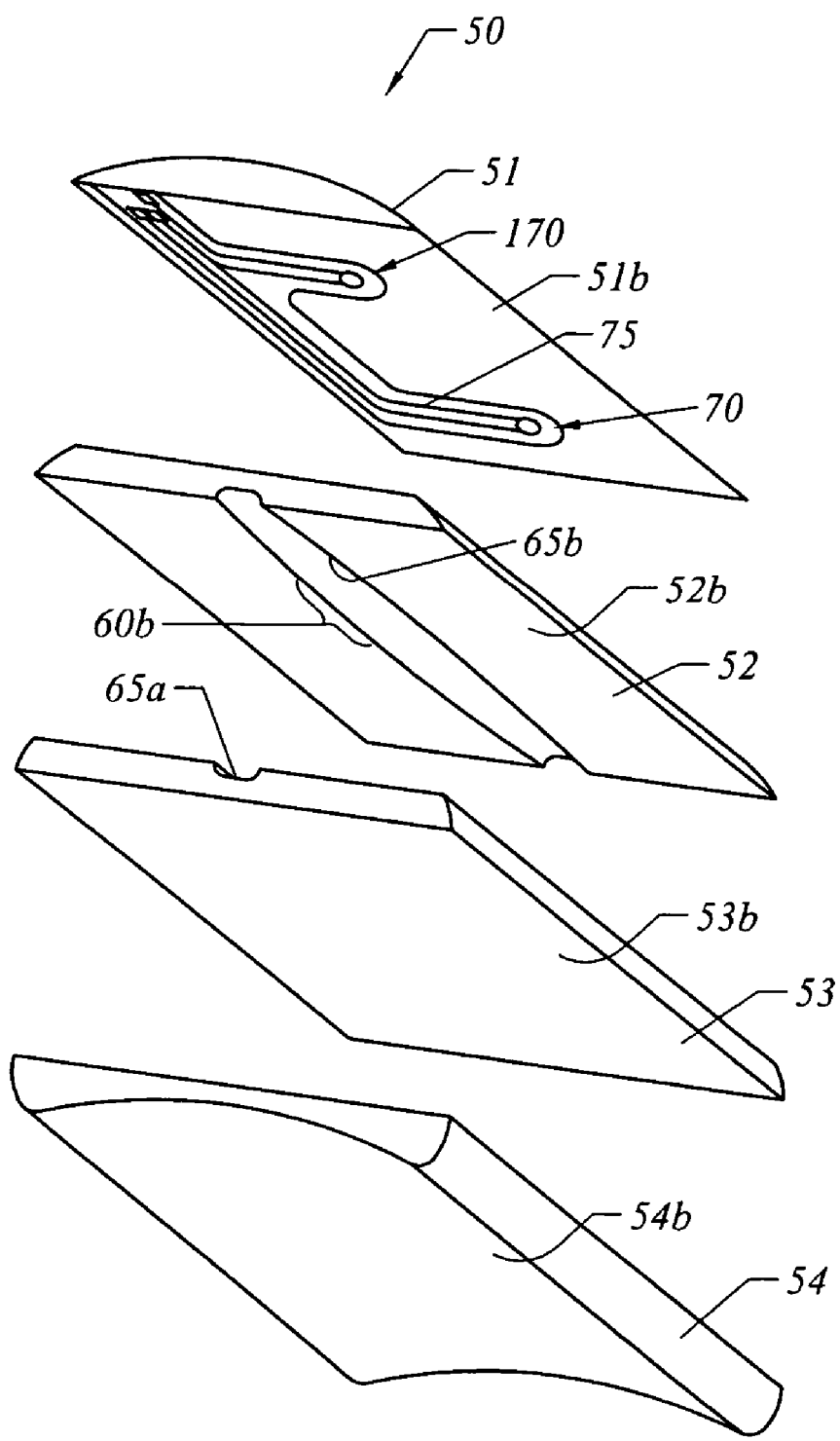
FIG. 6 is an exploded view of the same four layers shown in FIG. 5 showing the bottom surface of each of those four layers.

FIGS. 5 and 6 illustrate the four molded plastic layers 51–54, from above in FIG. 5 and from below in FIG. 6. The top layer 51 has an upper surface 51a shown in FIG. 5 and a lower surface 51b shown best in FIG. 6. The lower surface 51b carries light sources 70 and 170. Light sources 70 and 170 are energized by flex circuits 75 and 175, respectively. The top surface 52a of layer 52 is flat as shown in FIG. 5. Layer 52 is transparent. The lower surface 52b of layer 52 has a channel 65b formed therein. The central section of channel 65b is shown as 60b and forms the upper portion of test chamber 60. The central portion 60b of channel 65b is a slightly widened segment of channel 65b.

The upper surface 53a of layer 53 as shown in FIG. 5 carries a channel 65a which cooperates with channel 65b to form a passageway through which fluid flows through test unit shown generally as 50. The central section 60a of channel 65a forms the lower half of test chamber 60. The glucose oxidase electrode 91 is carried in channel 65a and is positioned below and immediately adjacent to test chamber 60 formed by the central segments 60a and 60b of channel 65a and 65b, respectively. The glucose oxidase electrode 91 is energized by flex circuit 95. The lower surface 53b of layer 53 is flat as shown in FIG. 6. The upper surface 54a of layer 54 carries photodetectors 80 and 180, energized by flex circuits 85 and 185, respectively. The lower surface 54b of layer 54 is shown in FIG. 6. Surface 54b has a gentle curvature to conform to the forearm of the patient.

Figure 7:
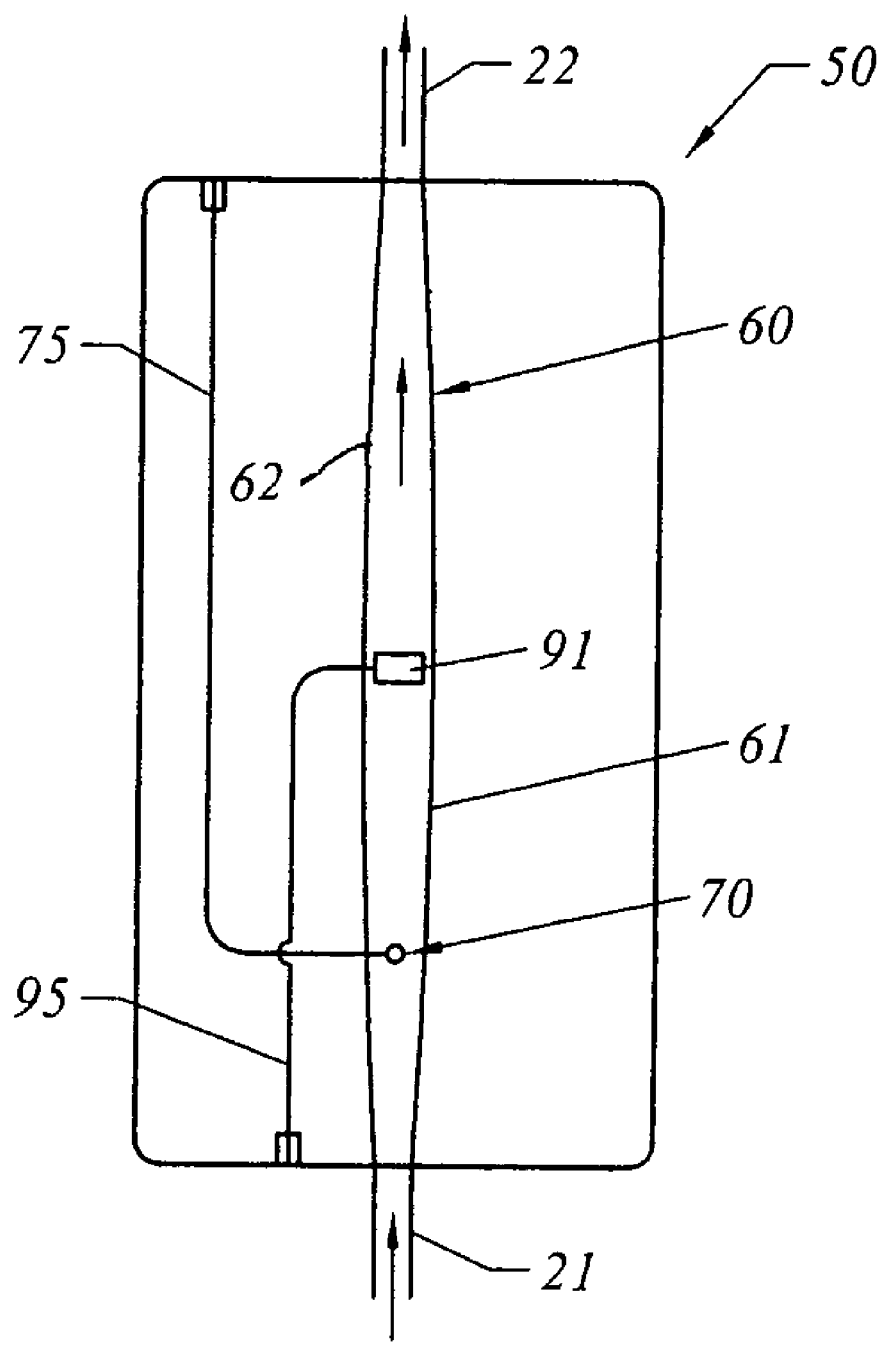
FIG. 7 is a schematic representation showing the relationship of a single light source and photodetector used with the test chamber.

As shown best in FIG. 7, which is a schematic representation looking downwardly at testing unit 50 (partially broken away), infusion fluid is shown flowing through first infusion line 21 and through testing chamber 60 and outwardly through second infusion line 22. As the peristaltic pump 40 continues to pump in the backward or reverse direction, the patient's blood is drawn into first infusion line 21 and flows into and through testing chamber 60. As the combination of infusion fluid and blood passes through test chamber 60, LED 70 is energized and the opacity of the fluid flowing past LED 70 is measured by the output of photodetector 80 (not visible in FIG. 7). When the opacity of the fluid moving through test chamber 60 is great enough to indicate the presence of an undiluted blood sample in chamber 60, the peristaltic pump is stopped, the glucose oxidase electrode 90 is energized and the blood glucose level is measured and immediately indicated on the screen 31 of monitor 30, as shown best on FIGS. 2 and 3. The peristaltic pump 40 is then energized to pump in the forward direction and the flow of infusion fluid into the patient's blood vessel is resumed. As shown in FIG. 7, a single light source and photodetector pair are utilized. When a single pair is utilized, the pair is preferably placed adjacent the distal end 61 of test chamber 60.

Figure 8:
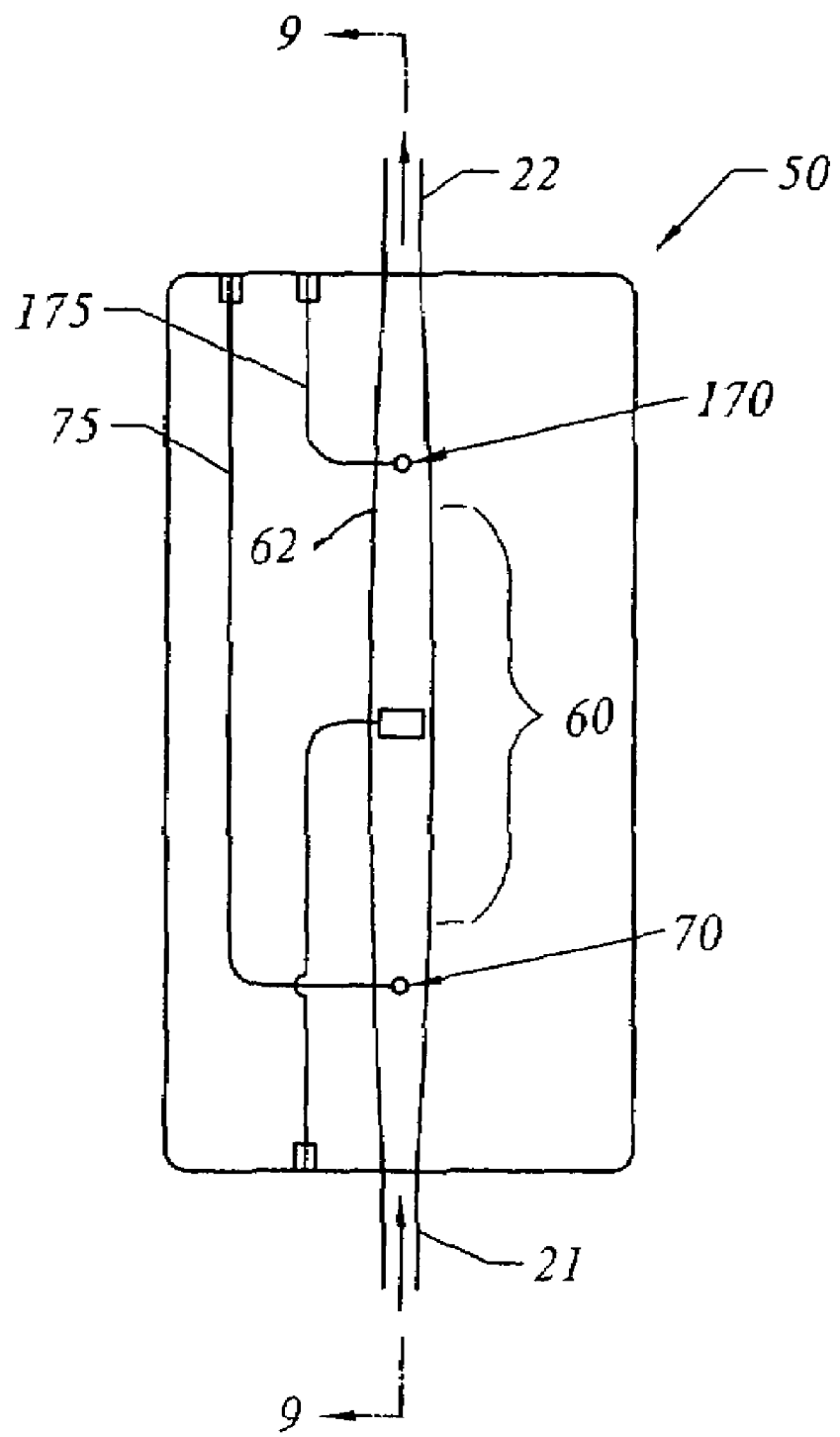
FIG. 8 is a schematic representation showing how two light sources are used on opposite ends of the test chamber.

In the preferred form of the invention, as shown in FIG. 8, a second light source 170 is placed adjacent the proximal end 62 of test chamber 60.

The use of two pairs of LEDs and photodetectors as shown in FIG. 8 provides a more accurate determination of the presence of an undiluted sample of blood in test chamber 60. As the detected opacity of the fluid entering test chamber 60 increases, the output of photodetectors 80 and 180 (FIGS. 9 and 12) decreases. When the opacity readings are equal and the opacities are sufficiently great to indicate the presence of blood, the peristaltic pump is stopped and the sample in test chamber 60 is tested. When the output of photocells 80 and 180 is equal, it indicates that the sample flowing through test chamber 60 is equally opaque adjacent each photocell 80 and 180. This indicates the presence of an undiluted blood sample in test chamber 60.

Figure 9:
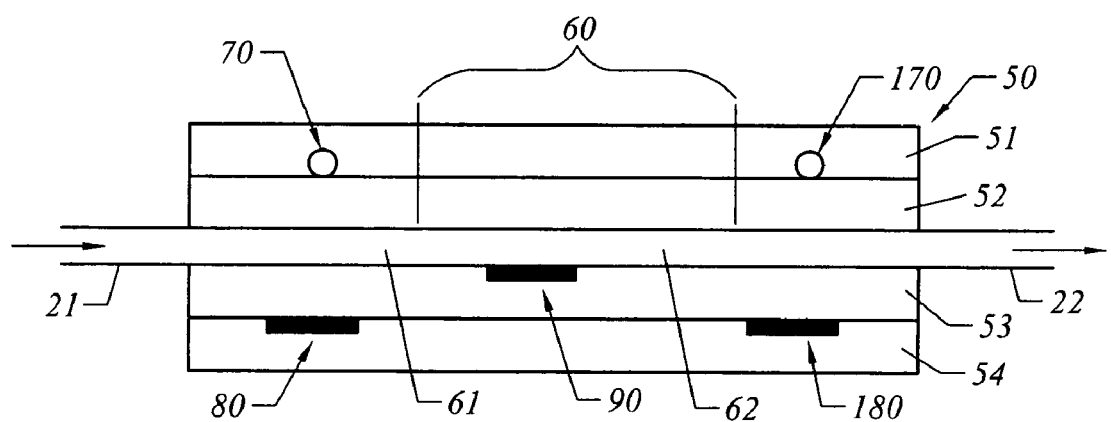
FIG. 9 is a schematic representation on the line 9—9 of FIG. 8 showing the relationship of the two pairs of LEDs/photodetectors to the test chamber.

FIG. 9 is a schematic taken on the line 9—9 of FIG. 8 showing the flow of fluid into first infusion line 21 through test chamber 60 and outwardly through second infusion line 22. The first LED 70 and photodetector 80 are shown adjacent the distal end 61 of chamber 60. Second LED 170 and photodetector 180 are shown located adjacent proximal end 62 of test chamber 60. The glucose oxidase electrode 90 is shown directly beneath and adjacent test chamber 60.

Figure 10:
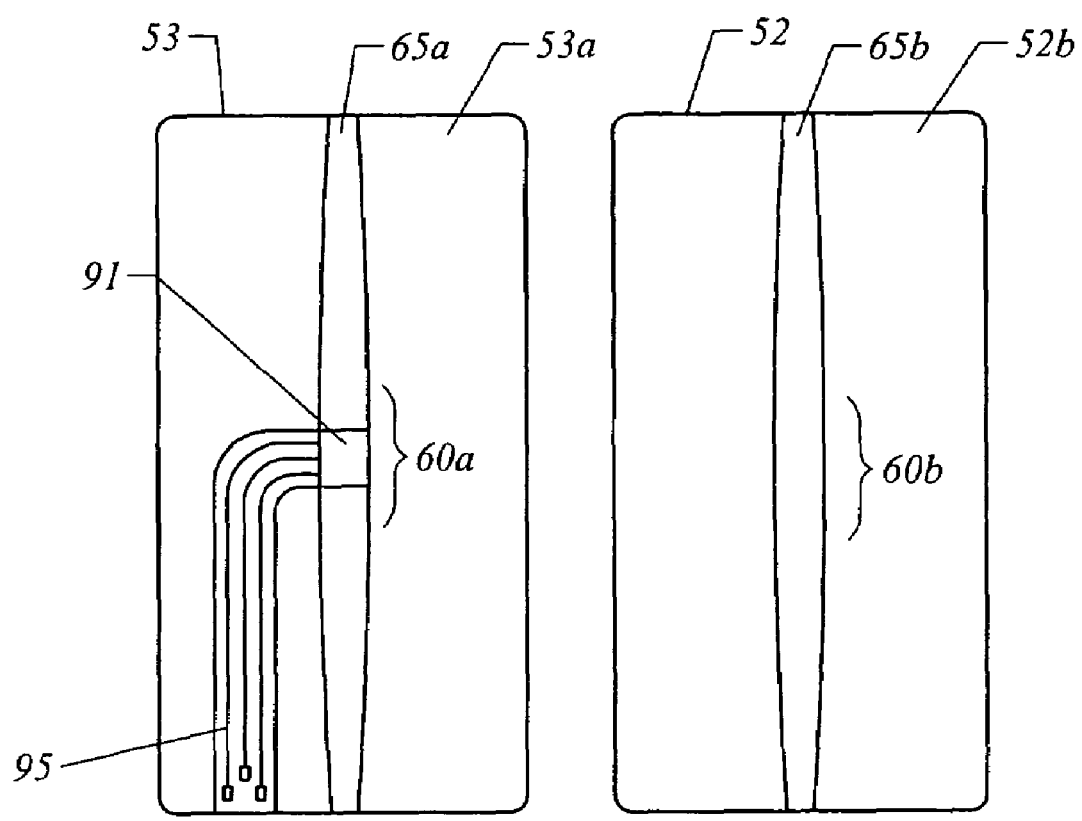
FIG. 10 is an illustration of the top surface of layer 53 and the bottom surface of layer 52 shown in side-by-side relationship.

FIG. 10 illustrates the upper surface 53a of layer 53 side-by-side with the lower surface 52b of layer 52. The channels 65a and 65b cooperate to form a single passageway through which infusion fluid and/or blood pass through testing unit 50 as described above. The central segment 60a of channel 65a and the central segment 60b of channel 65b cooperate to form test chamber 60. Glucose oxidase electrode 90 is shown connected to flex circuit 95.

FIG. 10 best illustrates the shape of test chamber 60, formed by channel segments 60a and 60b. The side walls of channels 65a and 65b are tapered only slightly in order to provide laminar flow across electrode 90 and to flush cells off the surface of electrode 90 between blood glucose testing sessions.

Figure 11:
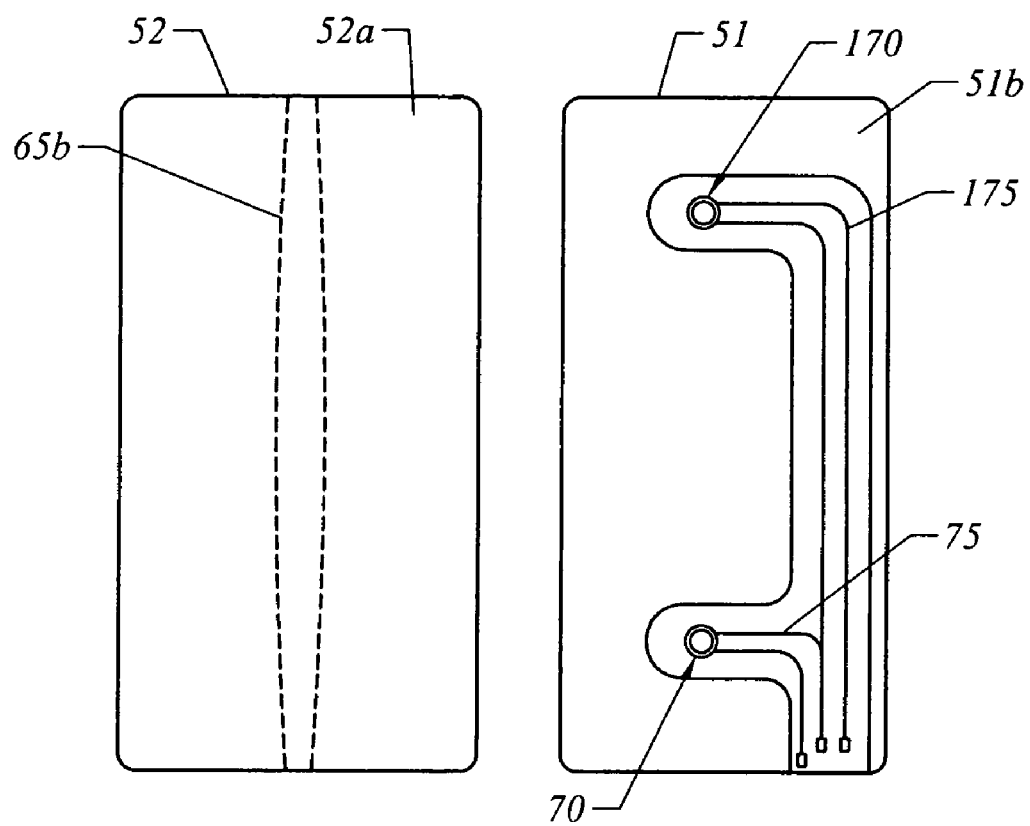
FIG. 11 is an illustration of the bottom surface of layer 51 and the upper surface of layer 52 shown in side-by-side relation to illustrate the relationship of the LEDs to the test chamber.

FIG. 11 illustrates the bottom surface 51b or layer 51 in side-by-side relationship with the top surface 52a of layer 52. Channel 65b is shown in phantom, since it is formed in the lower surface of layer 52 and not visible in FIG. 11. LEDs 70 and 170 are shown carried on the bottom surface 51b of layer 51 and energized by flex circuits 75 and 175.

Figure 12:
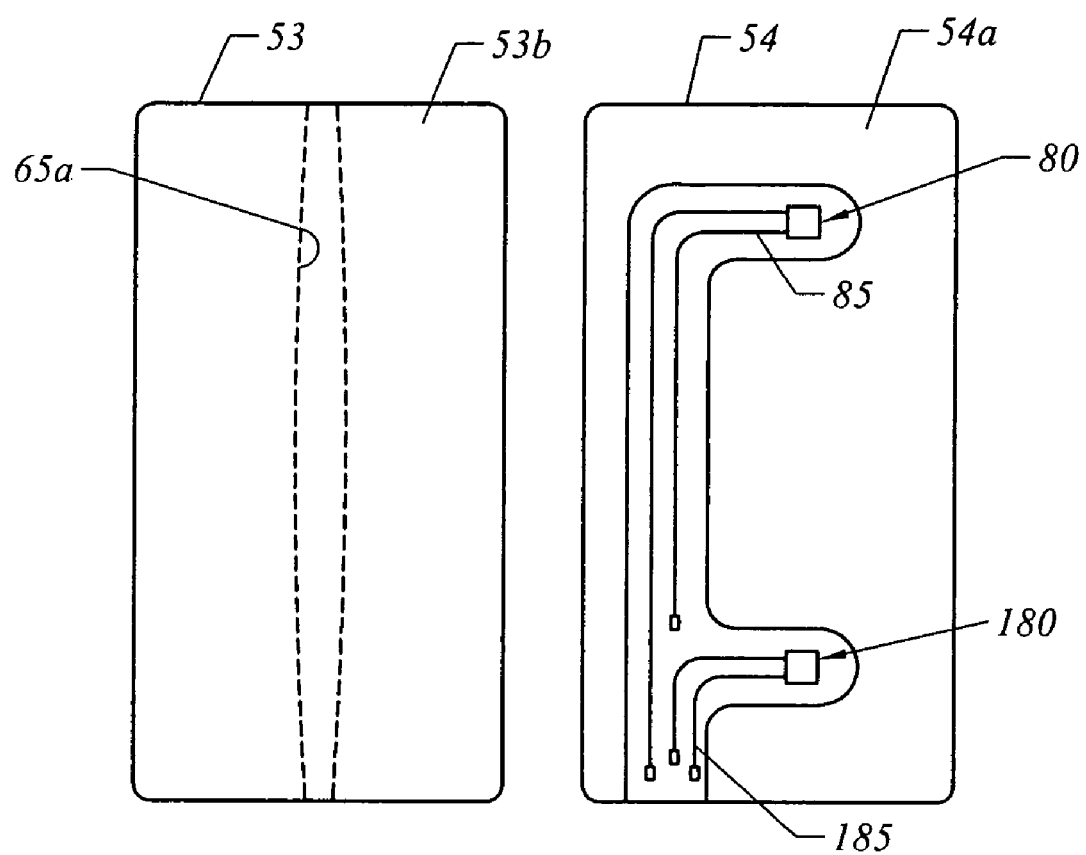
FIG. 12 is an illustration of the upper surface of layer 54 and the lower surface of layer 53 in side-by-side relationship to show the relationship of the two photodetectors relative to the test chamber.

FIG. 12 illustrates the upper surface 54a of layer 54 side-by-side with the lower surface 53b of layer 53. Channel 65a is shown in phantom in FIG. 12 since it is formed on the upper surface 53 and is not visible in FIG. 12. Photodetectors 80 and 180 are shown mounted on surface 54a along with flex circuits 85 and 185 which energize them.

The foregoing description of the invention has been presented for purposes of illustration and description and is not intended to be exhaustive or to limit the invention to the precise form disclosed. Modifications and variations are possible in light of the above teaching. The embodiments were chosen and described to best explain the principles of the invention and its practical application to thereby enable others skilled in the art to best use the invention in various embodiments and with various modifications suited to the particular use contemplated. The scope of the invention is to be defined by the following claims.

What is claimed is:

1. Apparatus for periodically and automatically testing a patient's blood glucose level, comprising:
    a disposable testing unit,
    a first infusion line having first and second ends connected at said first end to a catheter in a blood vessel of said patient and at said second end to said disposable testing unit,
    a second infusion line having first and second ends wherein said first end is connected to a source of infusion fluid and said second end is connected to said disposable testing unit, and
    a reversible peristaltic pump connected to said second infusion line, said pump adapted to either pump infusion fluid forwardly through said first and second infusion lines and said disposable testing unit into said patient blood vessel, to stop pumping, or to pump infusion fluid and blood backwardly from said patient blood vessel into and through said disposable testing unit,
    said disposable testing unit having a testing chamber in fluid communication with said infusion lines, a blood glucose testing means, and fluid opacity sensing means for sensing the opacity of said infusion fluid and blood pumped backwardly through said testing chamber wherein fluid opacity sensing means comprises a first light source and a first photodetector positioned adjacent a first end of said testing chamber and a second light source and a second photodetector positioned adjacent a second end of said testing chamber and for determining when said testing chamber is filled with undiluted blood from said patient blood vessel by comparing outputs from said first and second photodetectors, and when said outputs are equal and sufficiently great to indicate the presence of blood, an undiluted sample is present in said test chamber.

2. The apparatus of claim 1 wherein said first and second light sources are LEDs.

3. The apparatus of claim 1 wherein said testing unit comprises a plurality of molded layers and wherein said testing chamber is formed between two adjacent layers.

4. The apparatus of claim 3 wherein said adjacent layers are transparent and wherein said light source and photodetector are carried by said adjacent layers.

5. The apparatus of claim 1 wherein said testing unit comprises first, second, third and fourth molded plastic layers, wherein said test chamber is formed between said second and third layers, wherein said light sources are mounted between said first and second layers, and wherein said photodetectors are mounted between said third and fourth layers.

6. The apparatus of claim 5 further comprising flexible circuits carried on surfaces of said layers to energize said light sources and photodetectors.

\* \* \* \* \*